US006565845B2

(12) United States Patent
Cherksey et al.

(10) Patent No.: US 6,565,845 B2
(45) Date of Patent: *May 20, 2003

(54) METHOD FOR GENE TRANSFER TO THE CENTRAL NERVOUS SYSTEM

(75) Inventors: Bruce Cherksey, Hoboken, NJ (US); Louis R. Bucalo, San Francisco, CA (US)

(73) Assignees: Titan Pharmaceuticals, Inc., Somerville, NJ (US); New York University Medical Center, New York, NY (US)

( * ) Notice: Subject to any disclaimer, the term of this patent is extended or adjusted under 35 U.S.C. 154(b) by 23 days.

This patent is subject to a terminal disclaimer.

(21) Appl. No.: 09/730,328

(22) Filed: Dec. 4, 2000

(65) Prior Publication Data

US 2001/0003585 A1 Jun. 14, 2001

Related U.S. Application Data

(63) Continuation of application No. 08/629,308, filed on Apr. 8, 1996, now Pat. No. 6,210,664.

(51) Int. Cl.$^7$ ......................... A61K 48/00; C12N 15/00; C12N 15/63
(52) U.S. Cl. ................... 424/93.21; 514/44; 435/320.1; 435/91.4; 435/455; 424/489; 424/464; 424/493
(58) Field of Search ............................. 424/93.21, 93.2, 424/489, 464, 493; 514/44; 435/320.1, 325, 91.4

(56) References Cited

U.S. PATENT DOCUMENTS

| | | |
|---|---|---|
| 5,529,774 A | 6/1996 | Barba et al. |
| 5,618,531 A | 4/1997 | Cherksey |
| 5,656,481 A | 8/1997 | Baetge et al. |
| 5,688,773 A | 11/1997 | Chiocca et al. |
| 5,750,103 A | 5/1998 | Cherksey |
| 5,762,926 A | 6/1998 | Gage et al. |
| 5,906,817 A | 5/1999 | Moullier et al. |
| 6,210,664 B1 * | 4/2002 | Cherksey et al. |

FOREIGN PATENT DOCUMENTS

| | | |
|---|---|---|
| WO | WO 89/02468 | 3/1989 |
| WO | WO 92/06702 | 4/1992 |
| WO | WO 93/04167 | 3/1993 |

OTHER PUBLICATIONS

Armentano, D. et al. (May 1987). "Effect of Internal Viral Sequences on the Utility of Retroviral Vectors," *J. Virol.* 61(5):1647–1650.
Ausubel et al. (1995). *Current Protocols in Molecular Biology*, John Wiley and Sons, Inc. Title page and table of contents only.
Bitter, G.A. et al. (1987). "Expression and Secretion Vectors for Yeast," *Methods Enzymol.* 153:516–544.
Bjorklund and Stenevi, eds. (1985). *Neural Grafting in the Mammalian CNS*. pp. xix–xxiv Title page and table of contents only.
Borlongan, C.V. et al. (1996). "CNS Immunological Modulation of Neural Graft Rejection and Survival," *Neurological Res.* 18(4):297–304.
Chen, S. et al. (Mar. 1995). "Combination Gene Therapy for Liver Metasis of Colon Carcinoma In Vivo," *PNAS* 92:2577–2581.
Chowdhury, et al. (1989) *Miller, Advanced Res. on Animal Cell Technology*. Kluwer Academic Publishers pp. 315–327.
Colbere–Garapin, F. et al. (Jul. 25, 1981). "A New Dominant Hybrid Selective Marker for Higher Eukaryotic Cells," *J. Mol. Biol.* 150(1):1–14.
Cone, R.D. et al.(Oct. 1984). "High–Efficiency Gene Transfer into Mammalian Cells: Generation of Helper–Free Recombinant Retrovirus with Broad Mammalian Host Range," *PNAS* 81:6349–6353.
Consalvo, M. et al. (May 15, 1995). "5–Fluorocytosine–Induced Eradication of Murine Andocarcinomas Engineered to Express the Cytosine Deaminase Suicide Gene Requires Hose Immune Competence and Leaves an Efficient Memory," *J. Immun.* 154(10):5302–5312.
Culver, K.W. et al. (Mar. 1994). "Gene Therapy for the Treatment of Malignant Brain Tumors with in Vivo Tumor Transduction with the Herpes Simplex Thymidine Kinase Gene/Ganciclovir System," *Human Gene Therapy* 5(3):343–379.
Culver, K.W. et al. (1994). "Gene Therapy for Cancer," *TIG* 10(5):174–178.
Culver, K.W. et al. (Jun. 1992). "In Vivo Gene Transfer with Retroviral Vector–Producer Cells for Treatment of Experimental Brain Tumors," *Science* 256:1550–1552.
Dale, D.C. and Federman, D.D. (1995). *Scientific American Medicine*. Scientific American, Inc., New York, vol. 2:Chapter 7. (Title page and table of contents only).
Domb, A.J. et al. (1995). "Polymeric Carriers for Regional Drug Therapy," *J. Mol. Med. Today* 1(3):134–139.
DuBridge, R.B. et al. (1987). "Analysis of Mutation in Human Cells by Using an Epstein–Barr Virus Shuttle System," *Mol. Cell. Biol.* 7(1):379–387.
Freeman, S.M. et al. (Feb. 1996). "In Situ Use of Suicide Genes for Cancer Therapy," *Semin. Oncol.* 23(1):31–45.

(List continued on next page.)

Primary Examiner—Dave T. Nguyen
(74) Attorney, Agent, or Firm—Morrison & Foerster LLP

(57) ABSTRACT

The present invention relates to a method for implanting producer cells into the mammalian brain. The producer cells are engineered with a retroviral based recombinant vector encoding a tumorcidal factor or susceptibility factor that confers on tumor cells sensitivity to chemotherapeutic or radiotherapeutic agents. Prior to transplantation into the mammalian brain, the producer cells are first cultured in vitro on a support matrix to increase the long-term viability of the transplanted cells and to provide long-term functional benefit.

12 Claims, 2 Drawing Sheets

OTHER PUBLICATIONS

Gage, F.H. et al. (1988). "Human Amnion Membrane Matrix as a Substratum for Axonal Regeneration in the Central Nervous System," *Experimental Brain Research* 72(2):371–380.

Gilbert, J.C. et al. (1993). "Cell Transplantation of Genetically Altered Cells on Biodegradable Polymer Scaffolds in Syngeneic Rats," *Transplantation* 56(2):423–427.

Ghosh–Choudhury, G. et al. (Jun. 1987). "Protein IX, a Minor Component of the Human Adenovirus Capsid, is Essential for the Packaging of Full Length Genomes," *Embo. J.* 6(6):1733–1739.

Haraguchi et al. (1994). *Int. Cont. Aids.* 1994, 10/2, p. 114, No. PA0337.

Hartley, J.W. et al. (1976). "Naturally Occurring Murine Leukemia Viruses in Wild Mice: Characterization of a New ' Amphotropic Class," *J. Virology* 19(1):19–25.

Hartman, J.C. and Mulligan, R.C. (Nov. 1988). "Two Dominant–Acting Selectable Markers for Gene Transfer Studies in Mammalian Cells," *PNAS* 85:8047–8051.

Hock et al. (1989). "Expression of Human Adenosine Deaminase From Various Strong Promoters After Gene Transfer Into Human Hematpoietic Cell Lines," *Blood* 74(2):876–881.

Itakura, T. et al. (Jun. 1988). "Autotransplantation of the Superior Cervical Ganglion into the Brain," *J. Neurosurg.* 68:955–959.

Izquierdo, M. et al. (1997). "Gene Therapy in Brain Tumours: Implications of the Size of Glioblastoma on its Curability," *Acta Nerochirurgica Suppl.* 68:111–117.

Kantoff, P.W. et al. (Sep. 1986). "Correction of Adenosine Deaminase Deficiency in Cultured Human T and B Cells By Retrovirus–Mediated Gene Transfer," *PNAS* 83:6563–6567.

Kramm, C.M. et al. (1995). "Gene Therapy for Brain Tumors,"*Brain Pathology* 5(4):345–81.

Logan, J. and Shenk, T. (Jun. 1984). "Adenovirus Tripartite Leader Sequence Enhances Translation of mRNAs Late After Infection," *PNAS* 81:3655–3659.

Lowy, I. et al.(Dec. 1980). "Isolation of Transforming DNA: Cloning the Hamster aprt Gene," *Cell* 22:817–823.

Mastrangelo, M.J. et al. (Feb. 1996). "Gene Therapy for Human Cancer: an Essay for Clinicians," *Semin. Oncol.* 23(1):4–21.

Miller, A.D. et al. (1989). "Improved Retroviral Vectors for Gene Transfer and Expression," *Biotechniques* 7(9):980–982, 984, 986 & 989–990.

Miller, A.D. (1990). "Retrovirus Packaging Cells," *Human Gene Ther.* 1:5–14.

Moolten, F.L. (1986). "Tumor Chemosensitivity Conferred by Inserted Herpes Thymidine Kinase Genes: Paradigm for a Prospective Cancer Control Strategy," *Cancer Research* 46:5276–5281.

Moullier, P. et al. (1993). "Continuous Systemic Secretion of a Lysosomal Enzyme by Genetically Modified Mouse Skin Fibroblasts," *Transplantation* 56(2):427–32.

Mullen, C.A. et al. (1994). "Tumors Expressing the Cytosine Deaminase Suicide Gene Can Be Eliminated in Vivo with 5–Fluorocytosine and Induce Protective Immunity to Wild Type Tumor," *Cancer Res.* 54:1503–1506.

Mulligan, R.C. and Berg, P. (1981). "Selection for Animal Cells that Express the *Escherichia Coli* Gene Coding for Xanthine–Guanine Phosphoribosyltransferase," *PNAS* 78(4):2072–2076.

Naughton, B. A. et al. (1992). "Long–Term Expression of a Retrovirally Introduced β–Galactosidase Gene in Rodent Cells Implanted In Vivo Using Biodegradable Polymer Meshes," *Som. Cell and Mol. Gen.* 18(5):451–462.

O'Hare, K. et al. (1981). "Transformation of Mouse Fibroblasts to Methotrexate Resistance by a Recombinant Plasmid Expressing a Prokaryotic Dihyrdrofolate Reductase," *PNAS* 78(3):1527–1531.

Oldfield et al. (1993). "Gene Therapy for the Treatment of Brain Tumors Using Intra–Tumoral Transduction with the Thymidine Kinase Gene and Intravenous Ganciclovir," *Hum. Gene Ther.* 4:39–69.

Pear, W. et al. (1993). "Production of High–Titer Helper–Free Retroviruses by Transient Transfection," *PNAS* 90:8392–8396.

Rolland. Particulate Carriers. 1993: Petrak:275–297.

Sambrook et al.. (1989). *Molecular Cloning: A Laboratory Manual.* Cold Spring Harbor Laboratory Press, New York, 2nd ed. pp. xi–xxxviii. (Title page and table of contents only).

Santerre, et al. (1984). "Expression of Prokaryotic Genes for Hygromycin B and G418 Resistance as Dominant–Selection Markers in Mouse L Cells," *Gene* 30:147–156.

(1991). *Sigma Cell Culture Catalog.* Sigma Chemical Co., St. Louis, pp. 162–163.

Szybalska and Szybalski (1962). "Genetics of Human Cell Lines, IV. DNA–Mediated Heritable Transformation of a Biochemical Trait," *PNAS* 48(12):2026–2034.

Tamiya, T. et al. (1995). "Transgene Inheritance and Retroviral Infection Contribute to the Efficiency of Gene Expression in Solid Tumors Inoculated with Retroviral Vector Producer Cells," *Gene Therapy* 2(8):531–8.

Tiberghien, P. (Aug. 1994). "Use of Suicide Gene in Gene Therapy," *J. Leukocyte Biol.* 56:203–209.

Tjuvajev, J. et al. (1995). "RG–2 Glioma Growth Attenuation and Severe Brain Edema Caused by Local Production of Interleukin–2 and Interferon–Gamma," *Cancer Res.* 55:1902–1910.

Wigler, M. et al. (May 1977). "Transfer of Purified Herpes Virus Thymidine Kinase Gene to Cultured Mouse Cells," *Cell* 11:223–232.

Wigler, M. et al. (Jun. 1980). "Transformation of Mammalian Cells with an Amplifiable Dominant–Acting Gene," *Proc. Natl. Acad. Sci. USA* 77(6):3567–3570.

* cited by examiner

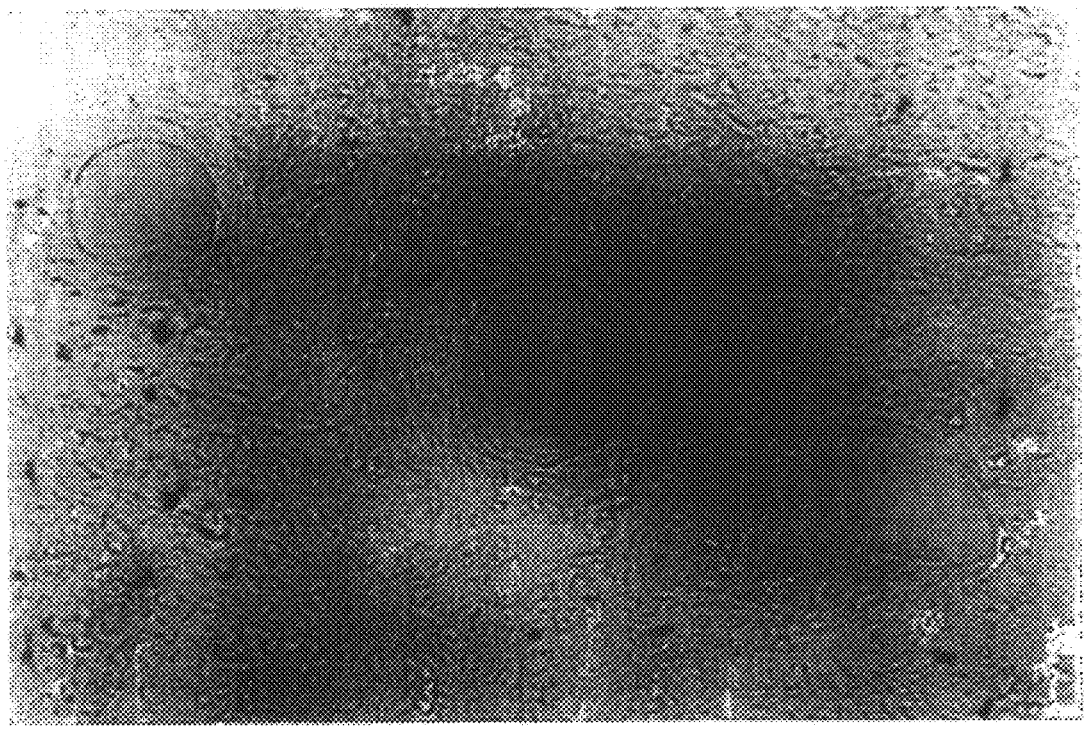
FIG._1
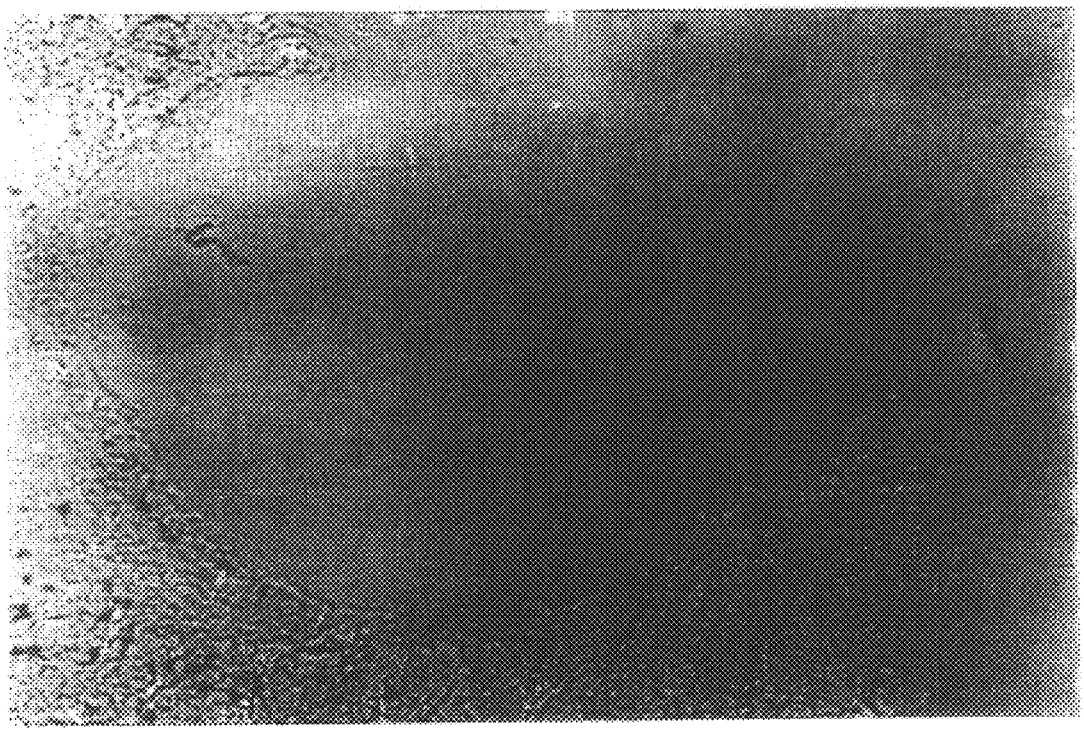
FIG._2

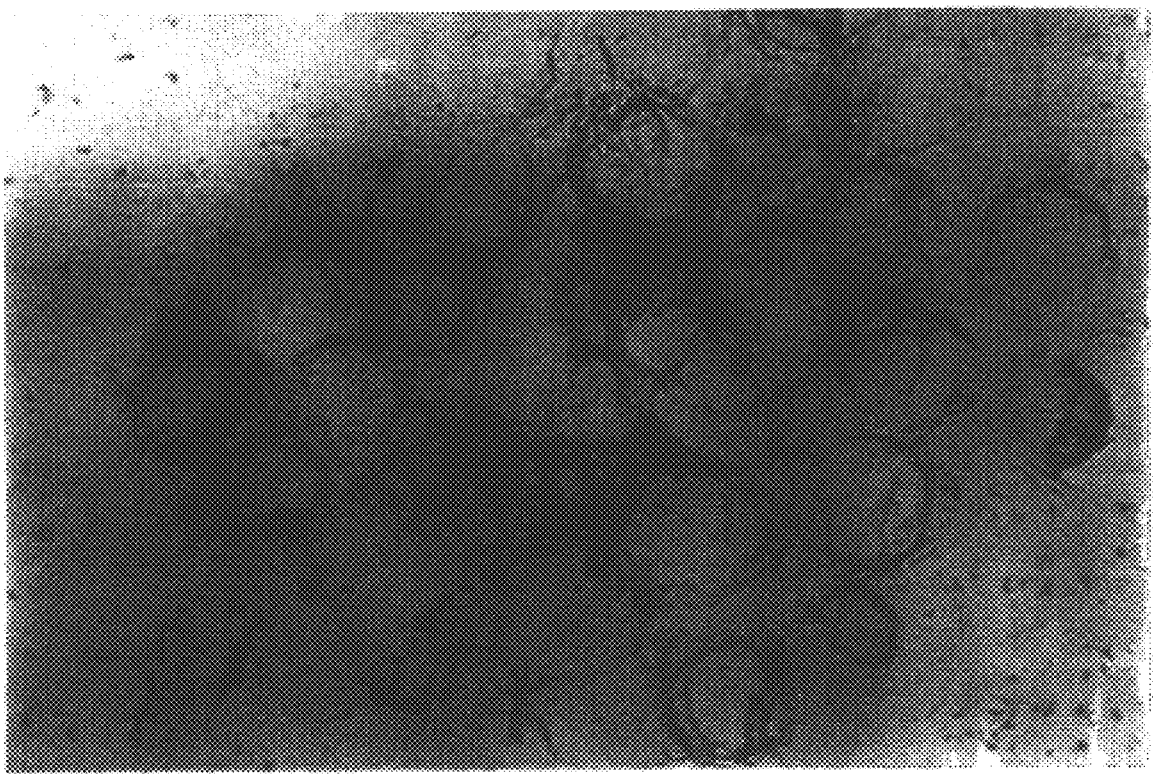
FIG._3

METHOD FOR GENE TRANSFER TO THE CENTRAL NERVOUS SYSTEM

CROSS REFERENCE TO RELATED APPLICATION

The present application is a continuation of U.S. patent application Ser. No. 08/629,308, filed April 8, 1996, now U.S. Pat. No. 3,210,664, the entire contents of which is hereby incorporated by reference.

INTRODUCTION

The present invention relates to a method for implanting producer cells into the mammalian brain. The producer cells are engineered with a retroviral based recombinant vector encoding a tumorcidal factor or susceptibility factor that confers on tumor cells sensitivity to chemotherapeutic or radiotherapeutic agents. Prior to transplantation into the mammalian brain, the producer cells are first cultured in vitro on a support matrix to increase the long-term viability of the transplanted cells and to provide long-term functional benefit.

BACKGROUND OF THE INVENTION

Brain tumors are the leading cause of cancer deaths in persons younger than 35 years. The incidence of central nervous system tumors is more than twice that of Hodgkin's disease, more than half that of melanoma and, in women, the frequency of mortality caused by tumors of the central nervous system is almost equivalent to that caused by ovarian cancer. In children, brain tumors are the most common solid tumor and are second only to leukemia as an overall cause of childhood cancer. (Dale, D. C. and Federman, D. D., 1995, Scientific American Medicine, Scientific American, Inc., New York, Chapter 7.) Most brain tumors are inoperable; and even for those brain tumors that are operable, the surgery is extremely difficult and frequently leads to neurological disorders.

The in vivo application of retroviral vector-mediated gene therapy has been applied to the treatment of brain tumors (Oldfield et al., 1993, Hum. Gene Ther.; 4:39–69; Culver et al., 1992 Science 256:1550–2). Perhaps, the most widely studied application of gene therapy utilizes retroviruses genetically engineered to express proteins that activate a relatively nontoxic pro drug to form a highly toxic agent. For example, retroviral producer cells expressing susceptibility factors have been transplanted into the brain tissue of patients in order to kill the tumor cells (Barba, D. et al., WO 93/04167). One particular application of the system utilizes the thymidine kinase gene of the Herpes simplex virus which confers sensitivity to anti-viral drugs such as ganciclovir and acyclovir (Barba et al., WO 93/04167; Moolten, F. L. et al., 1986, Cancer Research 46:5276–5281). The HSV-TK gene product catalyzes the phosphorylation of a number of nucleoside analogues which are poor substrates for the TK of mammalian cells. For example, the antiherpes drug acyclovir exhibits minimal toxicity to cells lacking HSV-TK activity, but is activated in cells expressing HSV-TK to a toxic form capable of inhibiting DNA synthesis and which has been shown to exhibit selective cytoxicity to cells expressing the HSV-TK gene.

One concern associated with the use of retroviral vector-mediated gene therapy is that the implanted producer cells might not continue to survive and/or express the therapeutic genes for the time periods required to achieve the maximum therapeutic benefit. It is generally known that cells directly implanted into the brain die within about a two to four week period (see, for example, Itukura, T. et al., 1988, J. Neurosurg. 68:955–959). In some instances, the adherence of cells to microcarriers, prior to implantation in vivo, has been shown to enhance the long-term viability of transplanted cells (Cherskey et al.; WO 9206702) but to date this method has not been successfully applied to retroviral producer cell lines.

SUMMARY OF THE INVENTION

The present invention relates to a method for transferring genes encoding a tumoridal factor or susceptibility factor to brain tumor cells. The method comprises the implantation of producer cells engineered with a retroviral based recombinant vector encoding a tumorcidal factor or susceptibility factor into the mammalian brain. The engineered producer cells produce infectious retroviral particles which are capable of infecting the neighboring brain tumor cells thereby rendering the tumor cells sensitive to chemotherapeutic or radiotherapeutic agents. Since the retroviral vector gene transfer system requires a proliferating target cell for integration and gene expression in the brain, the application of this system to brain tumors has the advantage that the retroviruses are targeted to the proliferating cells of the brain tumor, while the normal non-proliferating brain cells remain uninfected.

A number of genes encoding tumorcidal or susceptibility factors may be used in the practice of the invention. Such genes encode enzymes that can convert a relatively non-toxic producing into a highly toxic agent. Cells genetically engineered to express such genes essentially commit metabolic suicide in the presence of appropriate prodrug.

In an embodiment of the invention, the herpes simplex thymidine kinase (HSV-TK) gene may be engineered into the recombinant retroviral vectors. Any cells subsequently infected with the recombinant retroviruses, and expressing the HSV-TK gene, would become sensitive to chemotherapeutic agents such as acyclovir and ganciclovir. In another embodiment of the invention the cytosine deaminase (CD) gene may be engineered into recombinant retroviral vectors. Cells expressing the CD gene metabolize the relatively non-toxic producing 5-flourocytosine to the highly toxic 5-fluorouracil (Mullen, C A et al., 1994, Cancer Res. 54:1503–6).

The method of the present invention further comprises the culturing of the producer cells in vitro on a support matrix prior to implantation into the mammalian brain. The preadhesion of cells to microcarriers prior to implantation in the brain is designed to enhance the long-term viability of the transplanted cells and provide long term functional benefit.

The invention is based, in part, on the demonstration that preadhesion of producer cells to microcarriers prior to transplantation into the mammalian brain enhances the viability of the transplanted cells. In a particular embodiment, described herein, producer cells were transplanted into the brains of rats. The transplanted producer cells produce infectious retrovirus particles that have been genetically engineered to express the alkaline phosphatase gene. Results demonstrate the successful long term expression of the alkaline phosphatase gene in the brain of the transplanted animal.

DESCRIPTION OF THE DRAWINGS

FIG. 1. Section from the brains of rats implanted with non-transfected cells on microcarrier beads (20× magnification). Little or no staining is seen surrounding the beads.

FIG. 2. Section from the brains of rats implanted with transfected cells, no microcarriers (20× magnification). No staining is seen in the section.

FIG. 3. Section from the brains of rats implanted 30 days earlier with cells transfected with alkaline phosphatase gene plasmid on microcarrier beads (lox magnification). High density of darkly staining material (cells) are seen.

DETAILED DESCRIPTION OF THE INVENTION

The present invention relates to a method for treating brain tumors comprising the implantation, into the mammalian brain, of producer cells engineered with a retroviral based recombinant vector encoding a tumoricidal factor or susceptibility factor. The producer cells produce infectious retroviral particles which are capable of infecting brain tumor cells thereby rendering those tumor cells sensitive to chemotherapeutic agents. The long-term viability of the producer cells may be enhanced through the in vitro culturing of the producer cells on a support matrix prior to implantation.

In particular, it has been demonstrated that DNA of interest can be efficiently and stably introduced into "producer cells" which are subsequently transferred to a support matrix that can be transplanted or grafted into a mammalian brain. The producer cells produce infectious retrovirus particles which can infect the brain tissue located in close proximity to the implanted producer cells. The infected brain tissue was shown to express the gene of interest up to 30 days after transplantation.

Retroviral Vectors

In order to express tumorcidal or susceptibility factors, the nucleotide sequences coding for such factors are inserted into an appropriate retroviral expression vector. Methods which are well known to those skilled in the art can be used to construct the recombinant retroviral vectors containing tumorcidal or susceptibility nucleotide coding sequences operatively associated with appropriate transcriptional/translational control signals. Construction of recombinant retroviral vectors containing the tumorcidal or susceptibility coding sequences may be generated using standard ligation and restriction techniques which are well understood in the art. See, for example, the techniques described in Sambrook et al., in Molecular Cloning: A Laboratory Manual, Cold Spring Harbor Laboratory, New York, 2d ed., 1989 and Auselbel et al., 1989, Current Protocols in Molecular Biology, Greene Publishing Associates & Wiley Interscience, N.Y.

A variety of retroviral based recombinant vectors may be utilized equally well by those skilled in the art. The recombinant vectors may contain varying amounts of retroviral sequences including retroviral long terminal repeats (LTRS), which are required for integration into the host genome, and packaging signals (psi) which are necessary for encapsidation of recombinant RNA transcripts of the provirus into mature viral particles. Particularly suitable retroviral vectors include but are not limited to those described in the following references each of which is incorporated by reference: SAX vectors (Kantoff P. W. et al., 1986, Proc. Natl. Acad. Sci. USA 83:6563); N2 vectors (D. Armentano et al., 1987, J. Virology 61:1647); LXSNA vectors (Miller A. D. et al., 1989, Biotechniques 7:980–990); and LASN vectors (Blood 72:876–81).

The recombinant vectors may also contain bacterial plasmid sequences necessary for conferring resistance to antibiotics such as ampicillin and tetracycline and sequences required for replication in bacteria. In addition, the recombinant vectors may contain selectable marker genes which may be used to identify stably transfected cells. The selectable marker in the recombinant vectors confers resistance to the selection and allows cells to stably integrate the recombinant retroviral expression vector into their chromosomes. This method may advantageously be used to identify successfully transfected producer cell lines which will subsequently produce infectious retrovirus particles.

A number of selection systems may be used, including but not limited to hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in HGPRT or APRT cells, respectively. Also, antimetabolite resistance can be used as the basis of selection for DHFR, which confers resistance to methotrexate (Wigler, et al., 1980, Natl. Acad. Sci. USA 77:3567; O'Hare, et al., 1981, Proc. Natl. Acad. Sci. USA 78:1527); GPT, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

A number of tumorcidal or susceptibility factors, may be used in the practice of the invention. Such factors are defined as those which confer on cells sensitivity to chemotherapeutic agents. In one particular embodiment of the invention, the HSV-TK gene is inserted into a recombinant retroviral vector. The HSV-TK coding region may be derived from a variety of publicly available clones (Wigler et al. 1977, Cell 11:223). The infection of tumor cells with such retroviral vectors confers on those cells sensitivity to drugs such as acyclovir and ganciclovir.

In accordance with the invention, nucleotide sequences encoding tumorcidal or susceptibility factors may be operatively associated with retroviral LTR promoter-enhancer signals. An operable linkage is one in which the LTR promoter/enhancer sequences and the tumorcidal or susceptibility gene are associated in such a way as to permit gene expression. Alternatively, other promoter/enhancer sequences may be utilized equally well by those skilled in the art, to provide for transcription of the inserted sequences. For instance, promoters/enhancers elements isolated from the genome of mammalian cells, from viruses permissive for growth in mammalian cells, or produced by recombinant DNA or synthetic techniques may be used to provide for transcription of the gene encoding the tumorcidal or susceptibility factor. Any of a number of suitable promoter/enhancer elements, including constitutive and inducible promoters, may be used in the expression vectors.

Specific initiation signals required for efficient translation of the inserted gene may also be included in the retroviral expression vectors. These exogenous translational control sequences which may include ATG initiation codon and adjacent sequences can be of a variety of origins, both natural and synthetic. In cases where the entire tumoricidal or susceptibility gene, including its own initiation codon and adjacent sequences, is inserted into the appropriate expression vector, no additional translational signals may be needed. However, in cases where only a portion of the tumoricidal or susceptibility coding sequence is inserted, exogenous translational control signals, including the ATG initiation must be in phase with the reading frame of the tumoricidal or susceptibility coding sequence to ensure translation of the entire insert. The efficiency of expression may be enhanced by the inclusion of appropriate transcription enhancer elements, transcription terminators, etc. (see Bitter et al., 1987, Methods in Enzymol. 153:516–544).

In a specific embodiment described herein, producer cells were transfected with a retroviral vector genetically engineered to contain the gene encoding alkaline phosphatase, under the control of the vector LTR and G418 resistance driven by the SV40 promoter. The transfected producer cells were attached to collagen-coated dextran microcarriers followed by transplantation into the rat brain. Histological studies performed 30 days post-implantation indicated long-term expression of the alkaline phosphatase gene in retrovirally infected cells.

Although recombinant retroviral vectors are the preferred vectors for use in the method of the present invention, other viral vectors may also be used to express tumoricidal or susceptibility genes. For example, adenovirus, adeno-associated virus, Epstein-Barr virus, papilloma virus, vaccinia virus, herpes virus and other human and animal viruses may be used to express tumoricidal or susceptibility factors in cells to be transplanted into the mammalian brain. For example, in cases where an adenovirus is used as an expression vector, the tumorcidal or susceptibility factor coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 and E3) will result in a recombinant virus that is viable and capable of expressing tumorcidal or susceptibility genes in infected host cells (e.g., See Logan & Shenk, 1984, Proc. Natl. Acad. Sci. (USA) 81:3655–3659).

Packaging Cell Lines

To produce transmissible retrovirus particles, the recombinant retroviral expression vectors are transfected into stable "producer" cell lines. Producer cell lines contain a stably integrated provirus expressing all of the retroviral functions required in trans for packaging of viral transcripts into mature virus particles. These include the group specific antigen (gag), envelop (env) and polymerase (pol) genes. The gag gene encodes the internal structural (nucleocapsid) proteins; the pol gene encodes the RNA directed DNA polymerase (reverse transcriptase); and the env gene encodes viral envelope glycoproteins. One essential feature of the stably integrated provirus is the lack of packaging sequences (the psi sequences) which normally provide the necessary signals in cis for packaging of viral transcripts. Therefore, transcripts arising from expression of the provirus are not packaged into viral particles, but rather, provide in trans the gene products required for packaging of viral particles.

Because retroviral vectors require cell division and DNA synthesis for efficient infection, integration and gene expression the "producer" cells are preferably actively growing cells. Such producer cells may include fibroblasts, neurons, glial cells, keratinocytes, hepatocytes, or any other mammalian cell capable of being transfected and implanted using the methods of the present invention.

A variety of producer cell lines may be employed for use in the method of the present invention. For example, already existing retroviral producer cell lines may be utilized in the practice of the invention. Such cell lines may include the BOSC23 (Pear, W. S. et al., 1993, Proc. Natl. Acad. Sci. USA, 90:8392–8396), Psi2 (Cone, R. D. et al., 1984, Proc. Natl. Acad. Sci. U.S.A. 81:6349–6353), Psi am (Hartley, J. W. et al., 1976, Journal of Virology 19:19–25) cell line or any other functionally equivalent producer cell line that provides gene products in trans necessary for viral packaging Alternatively, additional novel producer cell lines may be generated. To create additional producer cell lines, retroviral vectors which synthesize all the proteins required in trans for viral assembly are transfected into actively growing cells. A variety of transfection techniques which are well known to those skilled in the art, may be utilized to transfer the retroviral expression vectors into producer cell lines. Such techniques include calcium phosphate-DNA precipitation, DEAE-Dextran transfection electroporation, or liposome mediated DNA transfer.

The producer cells are subsequently transfected with the recombinant retroviral vectors which contain the tumoricidal or susceptibility genes and, optionally, DNA encoding a selectable marker. In instances where the recombinant vectors contain a selectable marker, a selection for transfected cells may be carried out prior to implantation.

In Vitro Culturing of Packaging Cell Lines

To increase the long term viability of the transplanted producer cells, the producer cells are first attached in vitro on a support matrix. Materials of which the support matrix can be comprised include those materials to which cells adhere following in vitro incubation, and on which cells can grow, and which can be implanted into the mammalian brain without producing a toxic reaction, or an inflammatory reaction which would destroy the implanted cells or otherwise interfere with their biological or therapeutic activity. Such materials may be synthetic or natural chemical substances or substances having a biological origin. The matrix materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentent, nylon, amyloses, gelatin, collagen, natural and modified polysaccharides, including dextrans and celluloses (e.g. nitrocellulose), agar, and magnetite. Either resorbable or non-resorbable materials may be used. Also intended are extracellular matrix materials, which are well-known in the art. Extracellular matrix materials may be obtained commercially or prepared by growing cells which secrete such a matrix, removing the secreting cells, and allowing the cells which are to be transplanted to interact with and adhere to the matrix. The matrix material on which the cells to be implanted grow, or with which the cells are mixed, may be an indigenous product of the implanted producer cells themselves. Thus, for example, the matrix material may be extracellular matrix or basement membrane material which is produced and secreted by the producer cells to be implanted.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans or growth factors, such as, for example, nerve growth factor (NGF). Alternatively, if the solid matrix to which the implanted cells are attached is constructed of porous material, the growth- or survival-promoting factor or factors may be incorporated into the matrix material, from which they would be slowly released after implantation in vivo.

When attached to the support according to the present invention, the cells used for transplantation are generally on the "outer surface" of the support. The support may be solid or porous. However, even in a porous support, the cells are in direct contact with the external milieu without an intervening membrane or other barrier. Thus, according to the present invention, the cells are considered to be on the "outer surface" of the support even though the surface to which they adhere may be in the form of internal folds or convolutions of the porous support material which are not at the exterior of the particle or bead itself.

The configuration of the support is preferably spherical, as in a bead, but may be cylindrical, elliptical, a flat sheet or strip, a needle or pin shape, and the like. A preferred form of support matrix is a glass bead. Another preferred bead is a polystyrene bead. Bead sizes may range from about 10 µm to 1 cm in diameter, preferably from about 90 to about 150 µm. For a description of various microcarrier beads, see, for example, *Fisher Biotech Source* 87–88, Fisher Scientific Co., 1987, pp. 72–75; *Sigma Cell Culture Catalog*, Sigma Chemical Co., St. Louis, 1991, pp. 162–163; *Ventrex Product Catalog*, Ventrex Laboratories, 1989; these references are hereby incorporated by reference. The upper limit on the bead size is dictated by the bead's stimulation of undesired host reactions such as gliosis, which may interfere with the function of the transplanted cells or cause damage to the surrounding brain tissue. Such limitations are readily determinable by one of skill in the art.

Transplantation of Packaging Cells

Producer cells expressing the tumorcidal or susceptibility genes are grown in vitro and attached to a support matrix. The method of the present invention includes the intracerebral grafting of producer cells containing the therapeutic gene of interest into the area of the brain affected by the tumor. Methods for transplanting cells into the brain are described in Neural Grafting in the Mammalian CNS, 1985, Bjorklund and Stenevi, eds and Gage et al., Brain Research, each of which are incorporated herein by reference. Procedures for transplanting cells into the brain include:

1) injecting the producer cells within the host brain or
2) preparing a cavity by surgical means for depositing the producer cells.

The producer cells may be injected into selected regions within the brain in close proximity to the area of the brain tumor. The producer cells are drawn up into a syringe and administered to the patient. Multiple injections may be made in the area of the tumor. Alternately, a cavity may be surgically prepared adjacent to the area of the brain affected by the tumor and the producer cells may be deposited into the cavity.

The number of cells needed to achieve the purposes of the present invention is variable depending on the size, age, weight of subject and size of brain tumor. The number of cells can be determined by one of skill in the art without undue experimentation. In an embodiment of the invention, described herein, genetically modified producer cells, attached to a support matrix were been implanted into the brains of rats. Histological studies indicate that retrovirus-mediated gene expression could be detected 30 days post-transplantation indicating the successful long term expression of retrovirus genes.

Having now generally described the invention, the same will be more readily understood through reference to the following examples which are provided by way of illustration, and are not intended to be limiting of the present invention, unless specified.

EXAMPLE

Long Term Retroviral Mediated Gene in the Mammalian Brain

The subsection below describes the transplantation of producer cells, attached to a support matrix, into the brains of rats. The transplanted producer cells produce infectious retrovirus particles that have been genetically engineered to express the alkaline phosphatase gene. The results demonstrate the successful long term expression of the alkaline phosphatase gene in the brain of the transplanted animal.

Materials and Methods

Animals and Cell Preparation

Male Sprague-Dawley (SD) rats were obtained from Taconic Farms (Germantown, N.Y.) at a weight of 120–150 g. The Bing cell line is an amphotropic counterpart to the BOSC23 cell line (W. Pear, et. al, Proc. Natl. Acad. Sci. (USA), 90, 8392–8396, 1993) isolated from the 293T (293tsa1609neo) human embryonic kidney cell line (R. B. DuBridge, at al, Mol. Cell Biol. 7, 379–387, 1987) that produced retroviral supernatants capable of infecting NIH3T3 cells at titres greater than $10^6$/ml following transient transfection. In the Bing cell line, amphotropic retrovirus constructs were introduced in order to package replication-defective retroviral vectors, such as LXSN-based retroviral vectors. The cell lines were maintained in high-glucose DMEM medium supplemented with 10% fetal calf serum (Hyclone) and antibiotics (penicillin-streptomycin solution, Sigma).

The alkaline phosphatase vector is based on LNSX retroviral construct (A. D. Miller, Human Gene Ther., 1, 5–14, 1990). It contains genes encoding alkaline phosphatase, under the control of the vector LTR and G418 resistance driven by the SV40 promoter.

To perform the transfection, $10^7$ Bing cells plated on a p100 petri dish were transfected with 10 ug of the alkaline phosphatase plasmid (purified on a Quiagen Maxi-prep column according to the manufacturer's instructions) using the standard calcium-phosphate transfection protocol (J. Sambrook, et al., Molecular Cloning, 2nd ed).

Seventy-two hours after transfection, the cells were harvested, aliquoted into fetal calf serum with 10% DMSO (Sigma) and placed at −70° C. for long-term storage. A portion of the transfected cells was transferred onto glass slides, fixed with 2% paraformaldehyde and stained for 1 hour with Nitro Blue Tetrazolilum (Sigma) at pH 8.5. Positive staining for alkaline phosphatase was observed in 30% of the Bing cells transfected with the alkaline phosphatase vector; no. specific staining was observed in control, uninfected Bing cells.

Attachment of Cells to Microcarriers

Prior to attachment to microcarriers, cells were washed three times into PC-1 (Hycor), a serum-free medium, and resuspended into PC-1. Collagen-coated dextran microcarriers (Cytodex® 3, 100–200 um) were sterilized by placing the beads in 10 ml of sterile distilled water per 1 gram of beads and heating to 121° C. for 15 min. The solution was allowed to cool to room temperature and the water was discarded. The microcarriers were then suspended into a small volume of culture medium and allowed to stand for 30 mins. The medium was removed and the beads (approximately 0.21 g) were added to the previously described cell preparation. The resulting mixture was shaken for 2 hours and an additional 4 mls of PC-1 was added. The culture flask was then incubated with periodic mixing overnight to allow the cells to adhere to he microcarriers. After incubation and prior to implantation, an aliquot was taken and reacted with Trypan blue to determine cell viability and the number of cells attached to the microcarriers was determined by microscopic examination. This procedure resulted in the attachment of approximately 5 to 7 cells to each microcarrier with a 95% or better cell viability.

Administration of Cells

Animals were anesthetized using sodium pentobarbital (40 mg/kg, ip) and surgery was performed under aseptic conditions. The cells were injected into caudate/putamen region of the brain using a stereotaxic injection. Four groups of three animals each were implanted with 1) non-transfected cells alone, 2) non-transfected cells on microcarriers, 3) transfected cells alone, and 4) transfected cells on microcarriers. The implant was placed (after correction) at 1.5 mm anterior to the bregma, 2.0 mm lateral and 5.0 mm below the surface of the dura. The jaw bar was at −3.3 mm. Stereotaxic coordinates were corrected for the individual animal using the position directly over the bregma as the zero-value coordinates. Dorsal-ventral values were from the surface of the dura mater. Once the needle had been properly placed, cells were injected at a rate of 1 $\mu$l/min until a final volume of 5 $\mu$l had been injected. A tight-fitting stylet was inserted into the bore of the needle to push through residual beads which may have adhered to the needle. The surgical site was closed using Clay-Adams 9 mm. wound clips.

Histologic Study

Rats were anesthetized with sodium pentobarbital, 60 mg/kg i.p. and animals perfused with 400 mls. of heparinized phosphate buffered saline following by perfusion with 400 mls of 1% glutaraldehyde/4% paraformaldehyde/0.1 M Na Phosphate, pH 7.2. Brains were removed and placed in 30% sucrose in PBS and frozen-sections of 28 $\mu$m or 50 $\mu$m prepared. Sections were transferred to numbered test-tubes containing PBS, placed on gelatin-coated slides and stained for alkaline phosphate by reaction for 30 minutes at room temperature with 5-bromo, 4-chloro, 3-indolyl phosphate/iodonitrotetrazolium (BCIP/INT) (Biomedia, Foster City, Calif.) producing a brown reaction product. Routine histology was performed on 10 $\mu$m paraffin sections stained with hematoxylin and eosin.

Results

Animals were sacrificed 30 days post-implantation and histologic studies performed. FIGS. 1–3 illustrate the results obtained in these studies.

Sections from the brains of rats implanted with non-transfected cells without microcarriers exhibited no BCIP/INT positive material. Sections, taken at the transplant site, of brains from rats which had been administered transfected cells implanted without microcarriers showed little or no BCIP/INT positive material (FIG. 2).

To rule out the possibility that the microcarriers themselves produced a staining artifact, non-transfected cells implanted on microcarriers were also examined. FIG. 1 shows a typical section taken at the implant site. The lack of staining by the chromogen BCIP/INT indicates that the Cytodex® microcarriers do not contribute to the staining pattern seen in FIG. 3.

When cells were implanted with Cytodex® microcarriers and the histology performed 30 days later, a different pattern emerged. FIG. 3 shows a section at 20× magnification from the brain of a rat implanted 30 days earlier with CaK8p7 cells transfected with alkaline phosphatase gene plasmid. Staining with BCIP/INT reveals numerous cells at or near the bead surface which are positive for alkaline phosphatase. This is in sharp contrast to cells implanted without the microcarriers (FIG. 2).

The results obtained in these studies demonstrate the preadhesion of cells to microcarriers prior to implantation enhances the viability of the implanted cells and prolongs therapeutic window of gene therapy. When applied to the producer cell methodology, this prolonged response should maximize its therapeutic efficacy by increasing the gene delivery to the CNS.

What is claimed is:

1. A method for killing tumor cells in a mammalian brain comprising:
   (a) implanting an effective number of virus particle producer cells in proximity to the tumor cells in the brain so as to kill the tumor cells; wherein the implanted cells contain a viral expression vector; wherein the viral vector contains a gene encoding a tumoricidal or susceptibility factor; wherein the viral vector is preferentially expressed in proliferating cells; wherein the implanted cells are attached to the surface of a support matrix; and wherein the factor is expressed after implantation; and
   (b) exposing the tumor cells to a chemotherapeutic agent which is activated by the factor expressed from the viral vector, such that the activated chemotherapeutic agent is tumoricidal, thereby resulting in killing of the tumor cells.

2. A method for providing a tumoricidal or susceptibility factor to tumor cells in a mammalian brain comprising:
   (a) implanting an effective number of virus producer cells in proximity to the tumor cells in the brain; wherein the implanted cells contain a viral expression vector encoding a tumoricidal or susceptibility factor; wherein the viral vector is preferentially expressed in proliferating cells; wherein the implanted cells are attached to the surface of a support matrix; and wherein the factor is expressed after implantation.

3. The method of claim 2 wherein the method further comprises:
   (b) exposing the tumor cells to a chemotherapeutic agent which is activated by the factor expressed from the viral vector, such that the activated chemotherapeutic agent is tumoncidal.

4. The method of claim 2 wherein the method further comprises:
   (b) exposing the tumor cells to a radiotherapeutic agent which is activated by the factor expressed from the viral vector.

5. A method selected from the group consisting of the methods of claim 1 and claim 2 wherein the tumoricidal or susceptibility gene encodes a herpes simplex thymidine kinase.

6. A method selected from the group consisting of the methods of claim 1 and claim 2 wherein the tumoricidal or susceptibility gene encodes a cytosine deaminase.

7. A method selected from the group consisting of the methods of claim 1 and claim 2 wherein the viral vector contains a selectable marker.

8. A method selected from the group consisting of the methods of claim 1 and claim 2 wherein said support matrix is a porous or nonporous microbead.

9. A method of claim 8 wherein the microbead has a diameter from 90 to 150 μm.

10. A method selected from the group consisting of the methods of claim 1 and claim 2 wherein the support matrix is made of material selected from the group consisting of silicone oxide, polystyrene, polypropylene, polyethylene, polycarbonate, polypentene, acrylonitrile polymer, nylon, natural polysaccharide, modified polysaccharide, gelatin, amylose, magnetite, hyaluronic acid, and extracellular matrix.

11. A method selected from the group consisting of the methods of claim 1 and claim 2 wherein the viral vector is an adenovirus vector.

12. A method selected from the group consisting of the methods of claim 1 and claim 2 wherein the viral vector is an adeno-associated virus vector.

\* \* \* \* \*